(12) United States Patent
Hofmeister et al.

(10) Patent No.: US 9,863,868 B2
(45) Date of Patent: Jan. 9, 2018

(54) ANALYSIS AND PURGING OF MATERIALS IN MANUFACTURING PROCESSES

(71) Applicant: H2Optx Inc., San Jose, CA (US)

(72) Inventors: Rudolf J. Hofmeister, San Jose, CA (US); Donald A. Ice, Milpitas, CA (US); Scott W. Tandy, Los Altos Hills, CA (US)

(73) Assignee: H2Optx Inc., San Jose, CA (US)

( * ) Notice: Subject to any disclaimer, the term of this patent is extended or adjusted under 35 U.S.C. 154(b) by 135 days.

(21) Appl. No.: 14/454,483

(22) Filed: Aug. 7, 2014

(65) Prior Publication Data

US 2016/0041087 A1 Feb. 11, 2016

(51) Int. Cl.
| | | |
|---|---|---|
| *G01N 1/10* | (2006.01) | |
| *G01N 21/11* | (2006.01) | |
| *G01N 21/03* | (2006.01) | |
| *G01N 21/31* | (2006.01) | |
| *G01N 21/65* | (2006.01) | |

(52) U.S. Cl.
CPC ............. *G01N 21/11* (2013.01); *G01N 21/03* (2013.01); *G01N 21/31* (2013.01); *G01N 21/65* (2013.01); *G01N 2021/115* (2013.01); *G01N 2201/022* (2013.01)

(58) Field of Classification Search
CPC ....... G01N 2201/022; G01N 2021/115; G01N 2021/8578; G01N 2021/135; G01N 2021/151; G01N 2021/152; G01N 2021/154; G01N 2021/155; G01N 2021/158; G01N 2021/0193; G01N 21/11; G01N 21/03; G01N 21/65; G01N 21/31; G01N 21/255; G01N 21/256; G01N 21/8057; G01N 21/85; G01N 21/658; G01N 21/35; G01N 21/359
USPC ......................................................... 356/246
See application file for complete search history.

(56) References Cited

U.S. PATENT DOCUMENTS

| | | | |
|---|---|---|---|
| 3,166,939 A | 1/1965 | Koeller et al. | |
| 4,900,435 A | 2/1990 | Anderson | |
| 5,096,471 A | 3/1992 | Sacks et al. | |
| 5,128,104 A * | 7/1992 | Murphy | .................. B01L 3/502 206/221 |
| 5,944,877 A | 8/1999 | O'Neil | |
| 7,113,265 B1 * | 9/2006 | Sarrazin | ................. G01N 21/85 356/244 |

(Continued)

OTHER PUBLICATIONS

International Search Report and Written Opinion dated Nov. 6, 2015 for International Patent Application No. PCT/US2015/044264 filed Aug. 7, 2015.

*Primary Examiner* — Sunghee Y Gray

(57) ABSTRACT

Various systems and methods of analyzing one or more properties of a sample are provided. The system includes a self-contained purging device having a sample holder and one or more analyzers for analyzing one or more properties of the sample. The purging device is configured to remove sample contained within the sample holder when an analysis is complete. In one embodiment the purging device is configured via an air pump having a tube in fluid communication with an air inlet of the sample holder, wherein the air pump is configured to deliver pressurized air to the air inlet and thereby purge the sample. The pressurized air is localized ambient air, and substantially free of contaminants. Methods and other systems are also described and illustrated.

23 Claims, 7 Drawing Sheets

(56) References Cited

U.S. PATENT DOCUMENTS

| | | | |
|---|---|---|---|
| 7,928,370 B2 | 4/2011 | Amirav et al. | |
| 2002/0061597 A1* | 5/2002 | Herpst | G01N 21/03 436/164 |
| 2004/0083028 A1* | 4/2004 | Vaidyanathan | B01J 8/10 700/269 |
| 2006/0208191 A1* | 9/2006 | Kessler | F26B 5/06 250/339.13 |
| 2006/0275541 A1* | 12/2006 | Weimer | G01N 21/658 427/96.1 |
| 2011/0194671 A1* | 8/2011 | Chen | G01N 23/12 378/44 |
| 2014/0079782 A1* | 3/2014 | York | A61K 9/0075 424/489 |
| 2014/0183362 A1* | 7/2014 | Islam | G01J 3/453 250/338.4 |

\* cited by examiner

ANALYSIS AND PURGING OF MATERIALS IN MANUFACTURING PROCESSES

BACKGROUND

1. Field of the Invention

Embodiments of the invention relate generally to in-process monitoring systems, and to methods of using such systems. More particularly, disclosed embodiments relate to in-process monitoring systems integrated into a production line and configured to analyze one or more properties of a sample as it is being produced, and methods of using such systems.

2. Description of the Related Art

During the manufacture of pharmaceuticals, fine chemicals, specialty chemicals and the like, a sample of the material is typically removed during production for testing to ensure that the material meets pre-established requirements. For example, a pharmaceutical powder may be tested to ensure that a sufficient amount of an active pharmaceutical ingredient is present. The testing of the material is usually performed "off-line," which can take hours or even days. By the time the test results are available, production of the material may already have been completed. If the test results do not meet specifications, the whole manufacturing lot must be discarded and must be produced again, which can be expensive, both in terms of time expended and wasted materials. Moreover, because there is a separation between the time of the actual material test and the manufacturing process itself, such test results may not be completely useful in assessing the reason for a failure.

Attempts have been made to design a testing device that may be integrated into the production process so that the material being produced is tested or analyzed while (or at substantially the same time) it is being manufactured. However, such attempts have not been satisfactory, primarily because the resulting devices are inaccurate or introduce additional problems. For example, such devices typically introduce contaminants into the manufactured material (e.g., by the use of compressed shop air), which causes inaccurate test results. Additionally, existing devices are not adequate because they are only capable of performing a subset of the desired tests and the testing of the material is incomplete.

SUMMARY

Disclosed embodiments are directed to systems and methods for analyzing samples in-process, and in substantially in real time. Thus, a material can be tested while it is being manufactured or produced. In this way, problems can be detected (and corrected) in a timely fashion, and in the context of a given production run. Moreover, disclosed embodiments provide the in-process testing in a manner that does not introduce contaminants into the production system.

In one embodiment, a system is provided for analyzing one or more properties of a sample of a material being produced in a production system. While the material being produced (and sampled) could include a variety of types, common examples would be pharmaceuticals, fine chemicals or specialty chemicals. The example system includes a self-contained purging device having a sample holder and one or more analyzers for analyzing one or more properties of a sample of the material that is obtained during the production process and placed in the sample holder. In operation, the system is integrated within the overall production system such that a sample of the material being produced is introduced into the sample holder. The one or more analyzers then perform a predetermined test on the retrieved sample. While any one of a number of different tests could be performed, current embodiments contemplate tests such as spectroscopy, moisture detection or measurement, particle size detection, and the like. When completed, the self-contained purging device expunges the sample from the sample holder. The purging device is "self-contained" in the sense that the purging function occurs without introducing any foreign materials or other components (excess humidity, oil, shop air, dust and the like) that are "external" to the production system, thereby avoiding the introduction of any contaminants into the sample holder (which could affect subsequent tests) or into the material being produced (which could compromise the viability of the production material). Because the production system is self contained, it can be used to monitor very precise particles over time, such as proteins being generated by bacteria, crystals, DNA, or whole cells.

The purging device can be implemented in a number of different ways. For example, in one embodiment the purging device is implemented so as to remove the sample from the sample container by way of pressurized air (or other appropriate gas). This embodiment includes, for example, an air pump having a tube in fluid communication with an air inlet of the sample holder. The air pump is configured to deliver "on demand" pressurized air to the air inlet that is sufficient to completely purge the material sample from the sample holder. Preferably, the air is "ambient" or localized air that is obtained local to the system and is thereby contaminant free. Optionally, the air can also be filtered to further eliminate the potential for contaminant introduction. Ideally, the delivered air is pressurized on demand (e.g., via the air pump), and thus isn't provided via external resources, such as external "shop" air or compressed air sources, which typically contain contaminants such as oil.

The purging device can be implemented using other purging techniques as well, again with the objective of completely purging the sample from the sample holder while avoiding the introduction of contaminants. For example, in one embodiment, the purging device includes a vibrating mechanism instead of (or in some embodiments, in addition to) an air pump. In this embodiment, mechanical vibration or movement is used to purge the sample from the holder (or to supplement the use of pressurized air for sample removal). Alternatively, purging could be provided via acoustic or sonic waves imposed on the sample. Other techniques could also be used, and/or combinations of the foregoing techniques.

Other embodiments are directed to methods for performing in-process, real time testing of a sample of a material under production, using systems of the type described above. For example, in one embodiment the method would involve the steps of retrieving a sample of a material being produced and placing it in a sample holder at an appropriate point of the production system. Next, and while production of the material continues, one or more analyzing steps are performed on the sample (e.g., spectroscopy, humidy, particle size, etc.) to evaluate desired properties. Once the analysis is completed, the sample is purged from the sample holder (or even optionally returned to the production system), such that the analysis is provided in a closed-loop, substantially real-time fashion. For example, if purging occurs via pressurized air, this step of the process might include actuating an air pump with ambient/localized or filtered air until air in a compression chamber is pressurized to a sufficient level and then purging the sample by delivering the pressurized air from an outlet of the air pump to an air inlet of the sample holder. The use of ambient and/or filtered air insures that the purged material, as well as the sample holder, is not contaminated as a result of the purging step, thereby maintaining the integrity of the tests performed, and the material being produced.

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

Additional features will be set forth in the description which follows, and in part will be obvious from the description, or may be learned by the practice of the teachings herein. Features of the invention may be realized and obtained by means of the instruments and combinations particularly pointed out in the appended claims. Features of the present invention will become more fully apparent from the following description and appended claims, or may be learned by the practice of the invention as set forth hereinafter.

The figures depict different embodiments for purposes of illustration only. One skilled in the art will readily recognize from the following discussion that alternative embodiments of the structures and methods illustrated herein may be employed without departing from the principles described herein.

DETAILED DESCRIPTION OF SOME EXAMPLE EMBODIMENTS

Embodiments of the present invention are directed to systems and methods for analyzing in-process samples in substantially real time while a manufacturing lot of material is being produced. Such systems and methods may reduce production time and prevent rejection of expensive batches of material such as pharmaceuticals, fine chemicals, and specialty chemicals.

Advantages of the system and methods described herein might include, but are not limited to: (1) providing a self-contained system that is integrated into the manufacturing line for real-time analysis of samples; (2) providing a system having a purging device that is capable of completely purging a sample from a sample holder in a manner that does not introduce contaminants; (3) providing a system that is easily serviced and cleaned to prevent cross-contamination of subsequent batches of production material; (4) providing a system in which the components used to purge a sample from a sample well are isolated (or self-contained) from the components used to analyze the sample; (5) providing a system that prevents a sample from entering and damaging other components of the system; and (6) providing a system that determines FDA-acceptable measurements and additional data that allows the material to be tested and validated during the actual production process.

As used in this specification and the appended claims, the singular forms "a," "an," and "the" include plural referents unless the content clearly dictates otherwise. Thus, for example, reference to a sample well having "an air inlet" includes sample wells having two or more air inlets.

Systems

Figure 1:
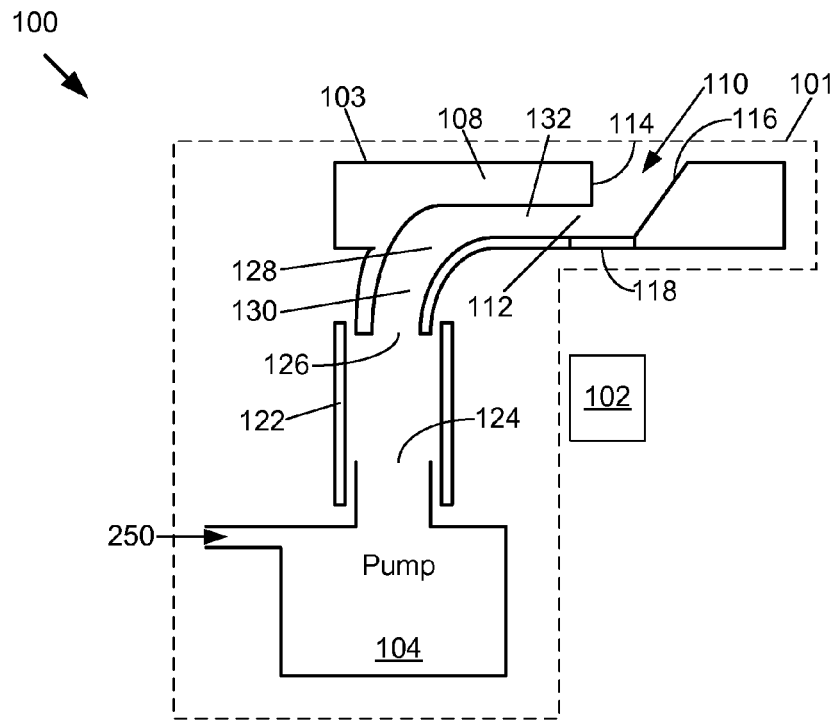
FIG. 1 is a schematic cross-sectional view of a system for analyzing one or more properties of a sample, according to one embodiment.

Referring to FIG. 1, a system 100 for in-process analysis of one or more properties of a sample is illustrated. In one embodiment, the system 100 is used to analyze one or more properties of a sample e.g., a powder or a liquid sample. The system is installed (or integrated) in a production line such that a sample of a material may be analyzed in substantially "real-time," which, as used herein, indicates that the analysis occurs while the material is being manufactured, produced or otherwise processed. The system 100 includes a self-contained purging device 101 configured to purge a material from a sample holder 103, one or more analyzers 102 configured to analyze a sample of material in the sample holder, and a power source (not shown) operably connected to the purging device 101 and one or more analyzers 102.

The sample holder 103 is configured to receive and retain a sample of the material during a time period corresponding to the manufacture of the material. The one or more analyzers 102 are configured to interact with the sample contained within the sample holder 103 and to analyze a property of the sample during the time period. The purging device 101 is operatively connected to the sample holder 103 and is configured, as described herein, to purge the sample from the sample holder 103 in a manner such that contaminants are not introduced into the sample holder.

The purging device 101 is "self-contained" or isolated from the one or more analyzers 102 to prevent the purging device 101 from interfering or contaminating the one or more analyzers 102. The system 100 may include one or more programmable controllers (not shown) for controlling each of the above components. The system 100 may also optionally include a housing (housing) to encase and protect the components therein.

FIGS. 1, 2A, 3A-3C and 4A-4C illustrate one embodiment of a purging device 101, here implemented so as to deliver pressurized air so as to purge material contained within a sample holder 103. Pressurized air is delivered via an air pump 104, as will be described in further detail below. Air pump 104 is an example of a source of pressurized air that is selectively delivered to the sample holder 103 so as to purge substantially the entire sample from the sample holder 103.

The sample holder 103 includes a body 108 formed of a chemically inert material that may withstand harsh cleaning substances such as detergent and solvents. In one embodiment, the body 108 is formed of stainless steel, substantially inert or non-reactive polymeric materials, or any other material that is suitable to the particular material being produced. In the illustrated embodiment, the sample holder 103 further includes a well 110 for retaining a sample. The well 110 includes a first wall 114 having an air inlet 112, a second wall 116 opposite the first wall 114, and a base 118 that permits appropriate access/interaction with the sample contained in the well 110 by an analyzer 102. For example, in one embodiment the base may be formed as a window that is optically clear, and through which the one or more analyzers 102 may analyze the sample via well-known spectrographic techniques, such as by excitation by a laser (not shown). Of course, depending on the analysis being performed, the base may include other forms so as to provide the appropriate access to the sample.

In the illustrated embodiment, the air inlet 112 is located on the first wall 114 such that pressurized air may reach the entire upper surface of the base 118 and thereby purge the sample from the base 118 and well 110. The air inlet 112 may be located on a lower portion of the first wall 114 and may span the width of the first wall 114. The air inlet 112 may be rectangular, circular, elliptical or any other appropriate cross-sectional shape. The first wall 114 of the well 110 may be substantially perpendicular to the base 118. The second wall 116 may have a surface that slopes away from the first wall 114 to facilitate removal of sample from the well 110. It will be appreciated that the configuration of the sample holder 103 might be shaped, sized and/or otherwise implemented in different ways so as to accommodate an alternate purging technique. For example, while the embodiment shown here is optimized for purging of sample material via pressurized air, other purging techniques might dictate differing sample holder configurations.

Figure 3A:
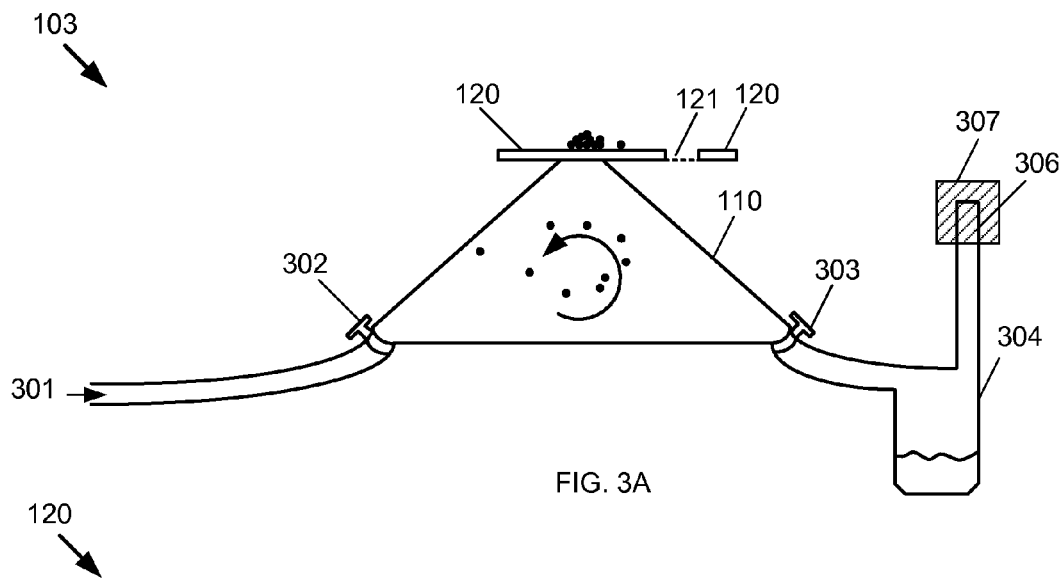
FIG. 3A is a schematic cross-sectional view of a sample holder having a movable cover with an aperture for allowing an in-process sample to fall into the sample well, according to one embodiment.
Figure 3B:
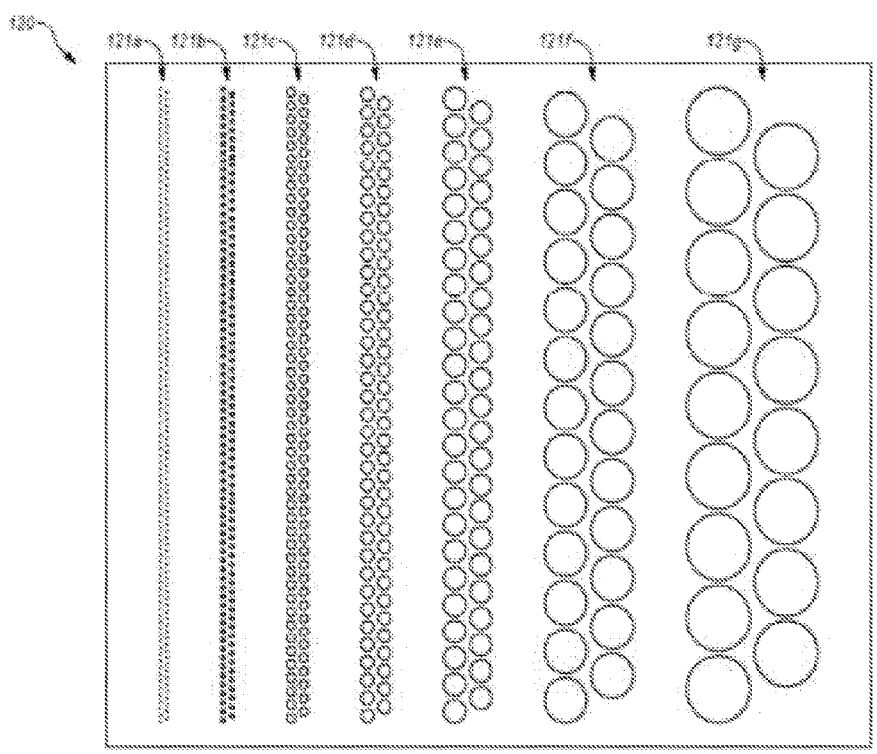
FIG. 3B is a top perspective view of one embodiment of a cover with a variable sieve retractable lid.

In embodiments illustrated in FIGS. 3A and 3B, the sample holder 103 further includes a movable cover 120 that may be used to retain a sample in the well 110. The cover 120 could be a lid, a powder bed, and the like. In one embodiment, the cover 120 may be actuated by, for example, air or a solenoid (e.g., via a programmable controller or the like). The cover 120 may be moved such that it uncovers the well 110 to allow the sample into the well 110 as well cover the well 110 to retain the sample in the well 110 or prevent particles from entering the well 110. In some embodiments, the sample holder 103 might include a vibrating mechanism that facilitates the rate at which particles enter the well 110. The cover 120 may be pivotally, hingedly or slideably attached to the body 108 of the sample holder 103. The cover 120 may be formed of a chemically inert material, e.g., stainless steel. In some embodiments, the cover 120 could include a rotating sieve for moving the particles into the well.

As illustrated in FIG. 3A, the cover may optionally include an aperture 121 smaller in diameter than the opening of the well 110. In these or other embodiments, the cover 120 and the aperture together move across the top of the well 110 so that particles pass through the aperture 121 into the well 110. The size of the aperture 121 can act as a filter so as to regulate the size of particles that are allowed to pass into the well 110. Additionally, the period of time during which the aperture 121 is over the well 110 can be varied (e.g., via the programmable controller) to vary, or otherwise control, the quantity of the sample that enters the well 110.

In some embodiments, the cover 120 might include a variable sieve that allow for particles of varying sizes to enter or leave the well 110. For example, FIG. 3B illustrates a top perspective view of an example embodiment of a cover 120. In the illustrated embodiment of FIG. 3B, the cover 120 includes one or more first-size apertures 121a, one or more second-size apertures 121b, one or more third-size apertures 121c, one or more fourth-size apertures 121d, one or more fifth-size apertures 121e, one or more sixth-size apertures 121f, and one or more seventh-size apertures 121g. The apertures 121a-121g have different sizes such that particles of different sizes can be selected for entry into or out of the well 110. For example, the first-size apertures 121a may have a diameter of 5 µm such that particles that are 5 µm or smaller may pass through the first-size apertures 121a; the second-size apertures 121b may have a diameter of 10 µm such that particles that are 10 µm or smaller may pass through the second-size apertures 121b; the third-size apertures 121c may have a diameter of 20 µm such that particles that are 20 µm or smaller may pass through the third-size apertures 121c; the fourth-size apertures 121d may have a diameter of 30 µm such that particles that are 30 µm or smaller may pass through the fourth-size apertures 121d; the fifth-size apertures 121e may have a diameter of 50 µm such that particles that are 50 µm or smaller may pass through the fifth-size apertures 121e; the sixth-size apertures 121f may have a diameter of 100 µm such that particles that are 100 µm or smaller may pass through the sixth-size apertures 121f; and the seventh-size apertures 121g may have a diameter of 150 µm such that particles that are 150 µm or smaller may pass through the seventh-size apertures 121g. The sizes and/or number of apertures may vary depending on the needs of a given application, and the above-listed sizes and number of apertures is merely one example.

Figure 3C:
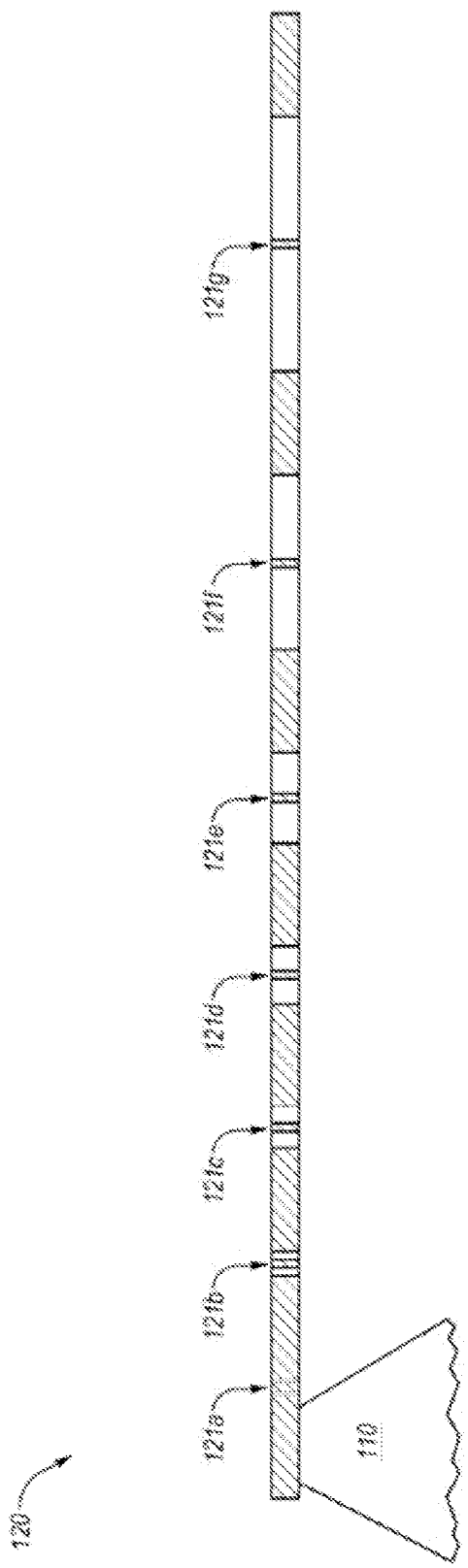
FIG. 3C is a side perspective view of one embodiment of a cover in the closed position.
Figure 4A:
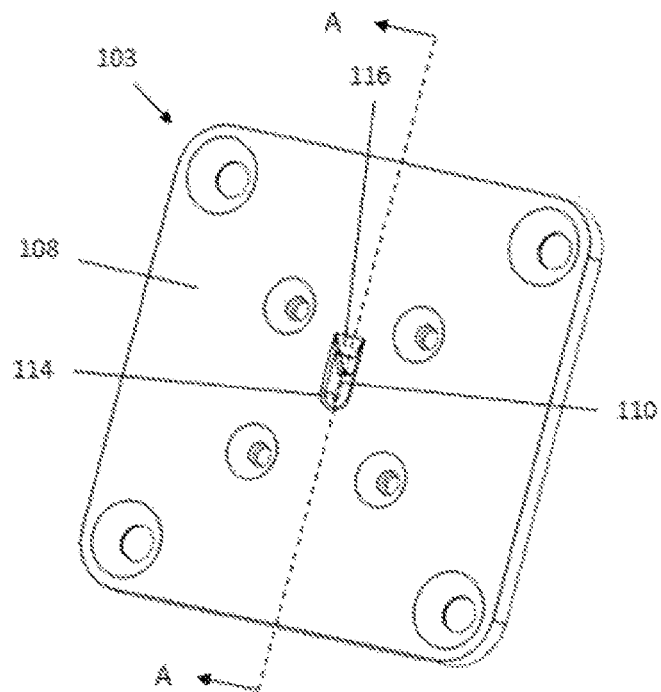
FIG. 4A is a top perspective view of a sample holder, according to another embodiment.
Figure 4B:
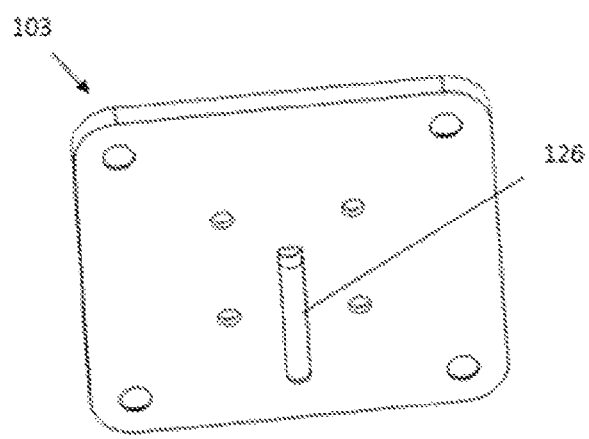
FIG. 4B is a bottom perspective view of a channel in the sample holder shown in FIG. 4A.
Figure 4C:
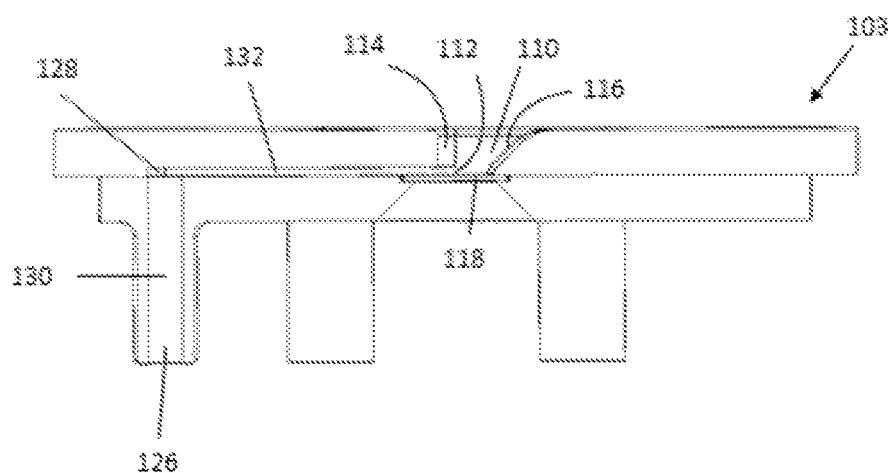
FIG. 4C is a cross-sectional view of the sample holder shown in FIG. 4A along line A-A.

As mentioned above, the cover 120 of FIG. 3B may be configured to interface with the well 110 of FIG. 3A such that different particle sizes are selected for entry into (or exit from) the well 110. FIG. 3C illustrates an example of the cover 120 of FIG. 3B positioned over the well 110. In the illustrated example of FIG. 3C, the cover 120 is in a closed position and can be moved selectively to the left such that specific apertures 121 of a desired size are positioned over the well 110, again, for example, under programmable control. Therefore, particles of a corresponding size are allowed into the well 110. The cover 120 can be moved back to the closed position once a desired amount of sample is deposited in the well 110.

If an application requires particles of most sizes to be deposited in the well 110, a larger aperture size, e.g., aperture 121g, can be positioned over the well. In this example, particles having a diameter of 150 µm or smaller will be allowed to pass into the well 110. Alternatively, or in addition, the cover 120 can be positioned such that smaller apertures 121 are positioned over the well 110. Compressed air can be pumped into the well 110 (e.g., via the pump 104) such that particles the same size as or smaller than the smaller apertures 121 exit the well 110 and larger particles are retained in the well 110.

Returning to FIG. 3A, in one embodiment, pressurized air is pumped through tubing 301 to the well 110. An incoming valve 302 going into the well 110 can be selectively opened (e.g., via programmable controller) to allow the air to pass through while keeping the exhaust valve 303 closed. This causes a disruption of sample particles to blow around inside the well 110. The analyzer 102 reads the well 110 continuously to average the Raman signal over about 100 mg. In some embodiments, the analyzer 102 integrates the signal instead of scanning the well 110. The pump 104 is turned off to let the particles settle. The analyzer 102 images the isolated particles. The analyzer 102 can use low numerical aperture (NA) optics, which may advantageously help create an average value over the sample.

Once the particles have been analyzed, a programmable controller or a user can open the exhaust valve 303 to purge the particles to the elutriation waste container 304. In some embodiments, the elutriation waste container 304 could also include a negative pressure mechanism for further clearing the particles from the well 110. Alternatively, the particles could be blown back into the feed frame and reintroduced into the production system. The waste container 304 can also contain a release valve 306 for releasing pressure generated by the pump 104 through the system that is covered by a filter 307 to prevent the particles from escaping.

In another embodiment, the system 100 in FIG. 1 may analyze crystals from fluid using a liquid purge with peristaltic pump. In one embodiment, the system 100 includes a well 110 where the crystals settle on a window such as the base 118 illustrated in FIG. 1 by gravity, centrifuge, electrostatic, or another attraction. The base 118 is transparent for viewing or otherwise detecting the crystals.

Since the distribution of crystals may be sparse, it is advantageous to have a well 110 with scanning capability under such circumstances. During operation, once the crystals have settled, the presence or concentration of the crystals can be analyzed using optical imaging, spectroscopic analysis, other techniques or a combination thereof. The pump can then be used to cause the fluid to flow over the window, thereby displacing the settled crystals. Once the crystals are displaced by the flow from the pump, the process may be repeated, as crystals from a subsequent sample settle onto the window 110.

In some embodiments, the system 100 includes a camera for capturing an image sparse field. The analyzer 102 in FIG. 1 analyzes the crystals. In one embodiment, the analyzer 102 identifies particles for image analysis. For example, the analyzer 102 performs an XY Raman scan of particles to identify composition and crystal morphology. This may be through direct Raman excitation to each particle to measure it. The analyzer 102 uses the image and any other information to analyze crystal size, shape, composition, etc.

Figure 2:
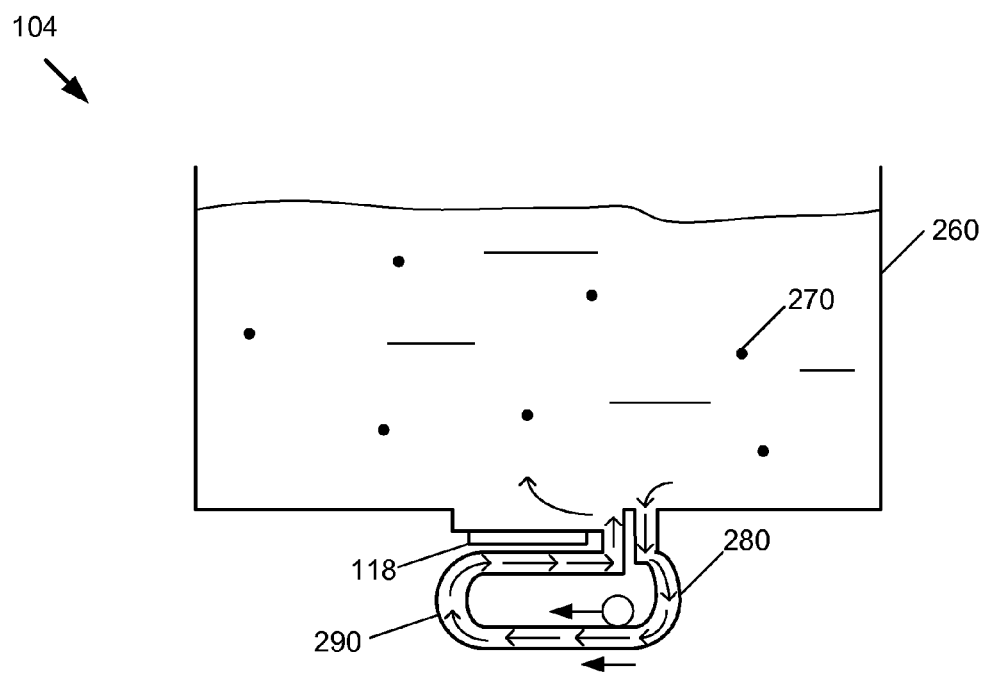
FIG. 2 is a schematic cross-sectional view of a peristaltic pump.

Turning to FIG. 2, the pump 104 of FIG. 1 may be a peristaltic pump 280 for use in an environment in which the particles to be measured or detected are contained in a liquid. The peristaltic pump 280 has the advantage that fluid from the manufacturing process and fluid from the instruments do not come into contact with each other, thereby avoiding contamination. The peristaltic pump 280 is used with liquid in a reaction or crystallization vessel 260 in this embodiment. The liquid includes crystals 270 or other reaction particles. The liquids feed into the peristaltic pump 280. The pump 280 displaces crystals after measurement, for example, using compressing tubing 290 that may be disposable. It is noted that the specific examples presented herein in the context of crystals in a liquid are more generally applicable to other operating environments. For example, the target material of the measurement process is allowed to settle from a fluid (i.e., liquid, air or another gas) onto the window. The material is then measured using the techniques described herein, and the pump is used to remove the measured material from the window and to allow material from a subsequent sample to settle onto the window to repeat the measurement process.

Returning now to an example of operation in the context of samples to be measured from an atmospheric environment, the air pump 104 of FIG. 1 is in fluid communication with the air inlet 112 of the well 110 in the sample holder 103. A connector 122 connects an outlet 124 of the air pump 104 to a channel 126 in the body 108 of the sample holder 103. In one embodiment, the connector 122 is a flexible tube formed from one or more chemically inert materials, such as silicone, PVC, polyurethane, fluoropolymers and/or thermoplastic elastomers. The channel 126 provides a passage through which the pressurized air may be delivered to the air inlet 112 of the well 110. The channel 126 may be curved or may have a turn 128 or an elbow having a first segment 130 angled at about 90 to 135 degrees relative to a second segment 132. For example, in the sample holder embodiment shown in FIGS. 1, 2, and 4C, the angle between the first and second segments 130 and 132 of the channel 126 is about 90 degrees. In one embodiment, the size (i.e., cross-section) of the channel 126 may be uniform from the connector 122 to the air inlet 112. In another embodiment, the size of the channel 126 may vary from the connector 122 to the air inlet 112, i.e., the channel 126 may taper in size from a small to large size or from a large to small size. In another embodiment, the shape of a cross-section of the channel 126 may change along the length of the channel 126, e.g., the cross section may change from circular to rectangular in shape or from rectangular to circular in shape. Again, cross-sectional shapes and/or sizes might be selected depending on the air-flow dynamics required to effect proper purging of a given material sample from the well of the sample holder.

Figure 5A:
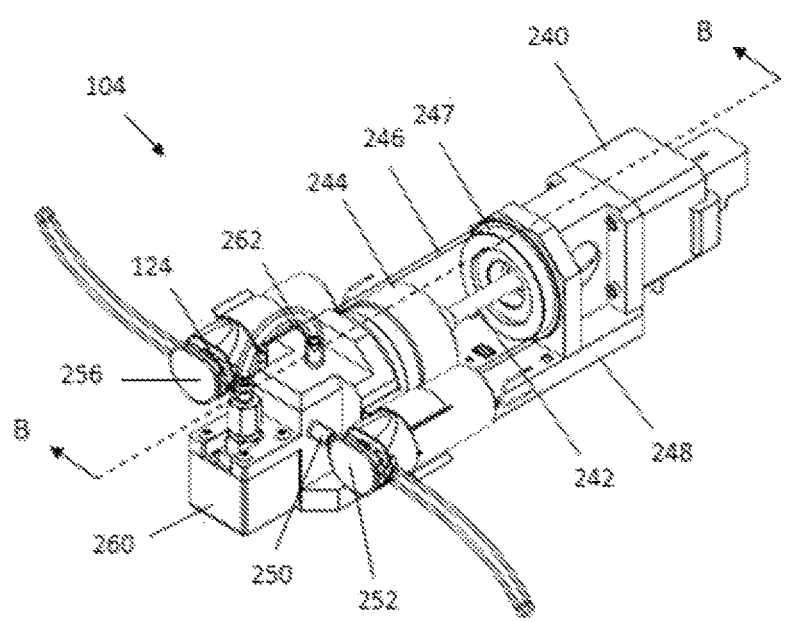
FIG. 5A is a front perspective view of an air pump, according to one embodiment.
Figure 5B:
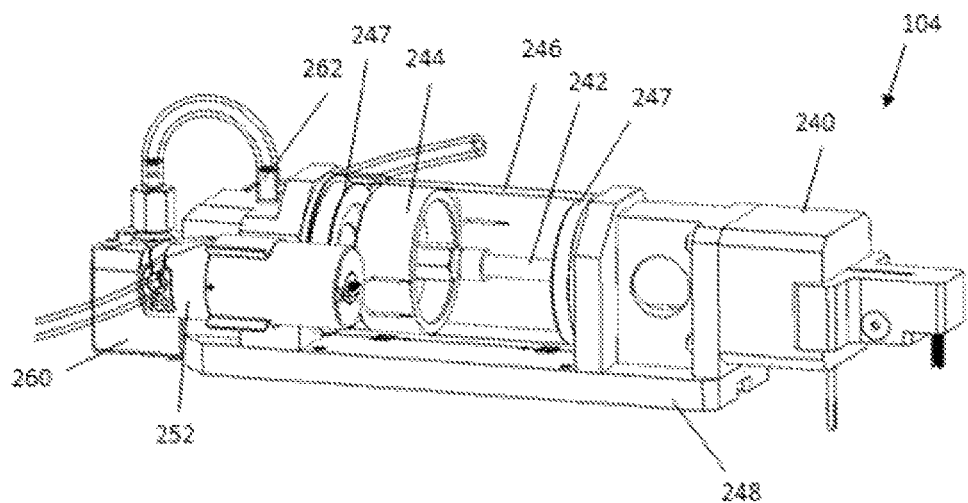
FIG. 5B is a side perspective view of the air pump shown in FIG. 5A.
Figure 5C:
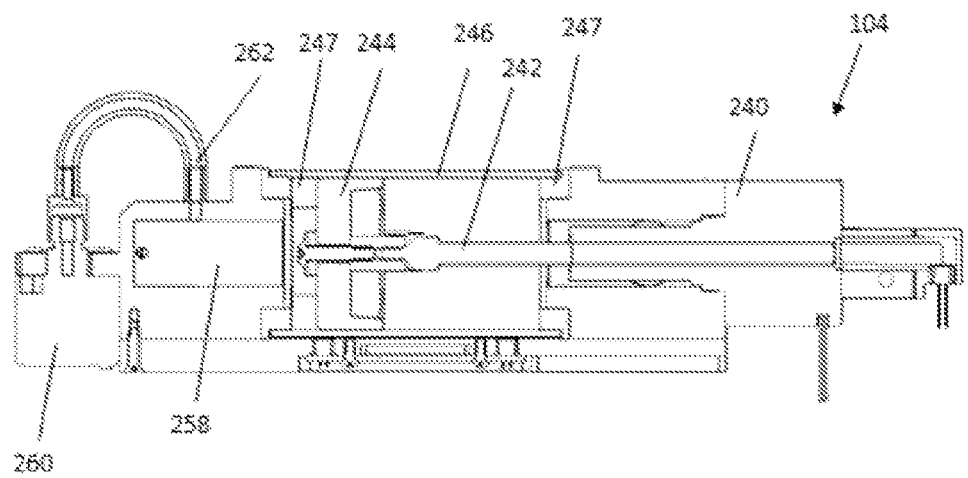
FIG. 5C is a cross-sectional view of the air pump shown in FIG. 5A along line B-B.

Referring again to FIG. 1, the air pump 104 of the purging device 101 is configured to deliver pressurized air to the air inlet 112 in the well 110. An exemplary embodiment of an air pump 104 that may be used in the system 100 is illustrated in FIGS. 5A-5C. In this example, the air pump 104 is linearly actuated and includes a self-lubricating piston rather than requiring oil lubrication which may contaminate production batches of material. The air pump 104 includes a drive mechanism having a motor 240 and one or more drive components (e.g., a screw-driven drive shaft 242) operably connected to a piston 244 in a reservoir 246 having one or more seals 247. Exemplary motors include a DC, a stepper or a solenoid motor. The motor may be powered by an external power source or a battery. In one embodiment, the piston 244 is formed from graphite and is self-lubricating. The air pump 104 may optionally be mounted on a support 248.

In the illustrated example, the air pump 104 further includes an air intake 250 having an air intake control valve 252 and an outlet 124 (or exhaust) having an outlet control valve 256. The air intake 250 may optionally include one or more filters for filtering out impurities in the air (i.e., ambient air) entering the pump 204. The outlet 124 is in fluid communication with the air inlet 112 of the sample holder 103 and may optionally include one or more filters. In an embodiment, the air intake control valve 252 and the outlet control valve 256 are solenoid-controlled pinch valves and are operated under programmable control via a controller (not shown).

The air pump 104 further includes a compression chamber 258 (see FIG. 5C) and an optional pressure sensor 260 that may be attached to an exit port 262 in the compression chamber 258. In an embodiment, the pressure sensor 260 is attached to the exit port 262 of the compression chamber 258 by, for example, a flexible tube. The pressure sensor 260 can be monitored via a controller so as to insure sufficient air pressure is available for purging of the material sample contained in the sample holder.

In another embodiment (not shown), a peristaltic pump may be used to deliver pressurized air to the air inlet 112 through tubing. An advantage of a peristaltic pump is that only the inner surface of the tubing comes into contact with the pressurized air which minimizes contamination of the air delivered to the inlet 112. Also, the air pump mechanism is protected from damage by ingress of a sample through the tubing.

While in the illustrated embodiment the purging device is configured so as to effect purging of the sample by way of pressurized air, it will be appreciated that other purging mechanisms could also be employed. For example, the pump 104 could be replaced with (or supplemented by) a device that causes the material to vibrate. The vibrating device could be located where the pump currently is or more directly beneath the well 110. Acoustic or sonic vibrations might also be employed to evacuate material from the sample holder. The purging can be performed or supplemented in certain embodiments using a mechanical transportation of the material from the well 110. The purging of the material from the well 110 can alternatively be facilitated using gravity by configuring the well 110 such that it is movable into a position from which the material can fall therefrom. In such embodiments, the various techniques for purging the material can be used in combination with an air pump.

Referring again to FIG. 1, the one or more analyzers 102 are located in close proximity to the base 118 of the well 110 such that the sample may be analyzed through the base 118. In an embodiment, the one or more analyzers 102 are located below the base 118. In another embodiment, the one or more analyzers 102 are coupled to the well 110 with relay optics or fiber optics. Exemplary analyzers 102 include, but are not limited to, a Raman spectrometer, a near infrared (NIR) spectrometer, a camera, an imaging particle analyzer and/or a differential calorimeter. Other analyzer types can also be employed, depending, for example, on the material under test and/or the types of tests needed.

Methods

In operation, the purging device 101 of the system 100 may be used to purge a sample from a well 110 after the sample is analyzed with one or more analyzers 102. In an exemplary method, an in-process sample from a batch of material being manufactured is placed into the well 110. The sample may, for example, fall into the well 110 by gravity as the batch of material moves past the well 110. In another example, the sample may fall into the well 110 through a sieve in the cover 120 or an aperture in the cover 121. This process may be facilitated via a vibrating device or by imposing negative pressure on the well 110. One or more properties of the sample are then analyzed. Both an outlet 124 and an air intake 250 of a pump 104 are closed, for example, via an input valve 302. In one embodiment, the air pump 104 of the air purging device 101 is activated by moving a piston 244 to an extended position until air in a compression chamber 258 is pressurized to a desired level, which can be monitored via pressure sensor 260. In another embodiment, a vibrating device causes the well 110 to vibrate. In some embodiments, the method results in an accurate active pharmaceutical ingredients (API) percentage in about 100 milliseconds (ms) to 1 second depending on how long the purging step below takes.

In one embodiment, after analysis is complete the sample is removed or purged from the well 110 by releasing pressurized air through the outlet 124 of the air pump 104 and delivering the pressured air to the air inlet 112 of the well 110. In another embodiment, the sample is purged by opening the exhaust valve 303 and activating the vibrating device. The purged sample may be added back to the batch of material being manufactured or disposed of in an elutriation waste container 304. In an embodiment, the release of pressured air through the outlet 124 can be controlled via activation of an outlet control valve 256. In an embodiment, air is delivered to the air inlet 112 at a suitable gas flow rate for a period of time (e.g., for one or more seconds to one or more minutes) until the sample is purged from the well 110. In another embodiment, modulated air is delivered to the air inlet 112 such that the gas flow rate is varied over a time period, e.g., for one or more seconds to one or more minutes. In another embodiment, one or more pulses of pressurized air are delivered to the air inlet 112 such that the pressurized air is cycled on and off one or more times. After removing the sample from the well 110, the pump outlet 124 is closed and the air intake 250 of the pump is opened to allow ambient air or a gas such as nitrogen or argon to enter the reservoir 246 of the air pump 104 as the piston 244 is moved back to a start position. Ambient air i.e., air that is local to the analysis system, is used instead of factory air which may have contaminants such as oil or particulates. The ambient air might also be filtered to further insure elimination of any contaminants. In this way, a material sample is completely purged from the sample container. Moreover, since elimination of the sample occurs in a manner that does not introduce contaminants into the sample container, further and continued analysis can be performed in-process and in substantially real-time. In this way, continuous and accurate analysis data can be obtained while the material is being produced. As such, corrective action can be taken as problems are detected, thereby reducing waste and production times.

In another exemplary method, a sample well 110 having a movable cover 120 (shown in FIGS. 2 and 3) is used with the system 100 to analyze an in-process sample from a manufacturing lot of material. In this embodiment, the air pump might also be used as a blower to mix or agitate a powder or liquid sample retained in a covered well. As the batch of material moves past the sample well 110, a measured amount of sample is deposited in the sample well and the movable cover is moved over an opening of the sample well or the sample is deposited through one or more apertures in the cover which is then moved so that a solid region of the cover is positioned over the opening of the sample well. Pressurized air is delivered to the sample well 110 such that the sample is mixed or agitated for a predetermined amount of time, such as about 100 ms. The sample is analyzed for one or more properties while being mixed. The sample may optionally be allowed to settle and then may be re-analyzed for one or more properties. After analyzing the sample, the sample may be sent (purged) to waste or may be added back to the batch of material moving past the sample well 110 as described above. This method may be used to measure the average properties of the sample, e.g., the Active Pharmaceutical Ingredient percent.

In an embodiment in which a small amount of a powdered sample is introduced into the covered well, individual particles may be analyzed and sized. In yet another embodiment, a liquid sample may be introduced to a sample well 110 with a cover 120. In this embodiment, air bubbles are introduced into the liquid sample and the velocity of the bubbles may be used to determine viscosity of the liquid sample.

Figure 6:
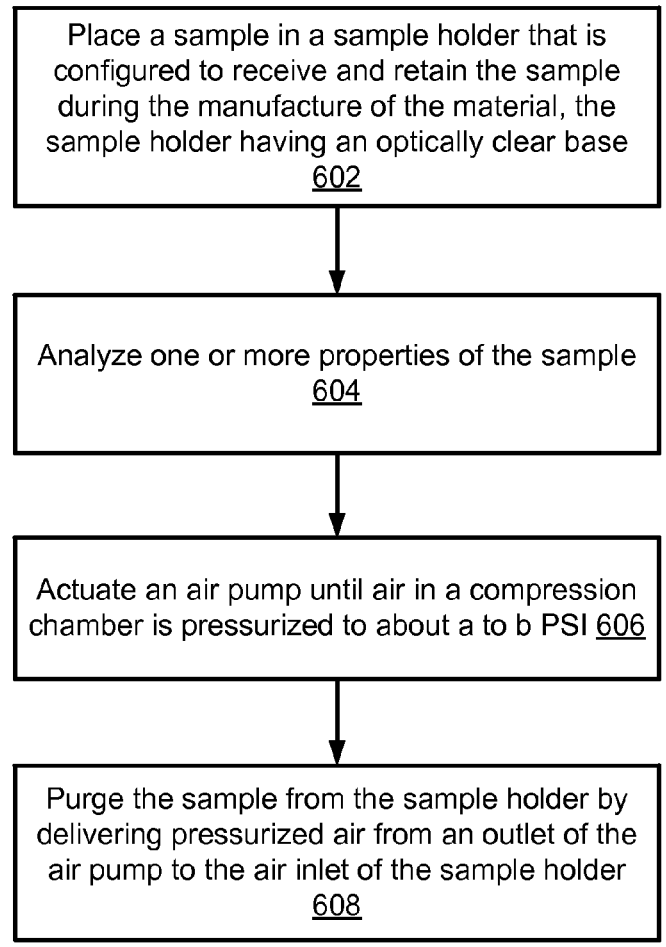
FIG. 6 is a flowchart illustrating one example of a method for purging a sample.

Turning now to FIG. 6, a flowchart 600 illustrating one example of a series of steps for purging a sample of material during a manufacturing process is illustrated. A sample is placed 602 in a sample holder 103 that is configured to receive and retain the sample during the manufacture of the material. In this particular illustration, the sample holder includes an optically clear base so as to accommodate analysis via, for example, spectrographic techniques. One or more properties of the sample are then analyzed, as is denoted at step 604. For example, an analyzer 102 could determine a percentage of active ingredients in the sample via spectrographic techniques.

Once analysis is complete, and while manufacture of the material continues, at process step 606 an air pump is actuated until air in a compression chamber is pressurized to a predetermined pressure (i.e., sufficient to evacuate the sample contained within the holder). As is represented at step 608, the sample is purged from the sample holder 103 by delivering pressurized air from an outlet 124 of the air pump 104 to the air inlet 112 of the sample holder 103. In some embodiments, the purged sample is collected in an elutriation waste container 304 or by reintroducing the sample back into the production system.

While the foregoing example process is described in the context of a purging device provided via pressurized air, alternate purging techniques could also be used in lieu of (or as a supplement to) pressurized air. Also, while not shown here, optional process steps might be added. For example, to facilitate analysis of the sample, pressurized air might be delivered to the sample holder to disturb the sample material in an appropriate manner.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, may be performed in reverse order when possible and may be performed sequentially as described above.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

What is claimed is:

1. A system for optically analyzing a powder sample in a continuous flow of powder, comprising:
    a sample holder, wherein the sample holder comprises:
        a top surface;
        a well, wherein in the well is defined by:
            an inlet within the top surface,
            a base opposite the inlet, wherein the base comprises an optical window;
            a first side wall between the top surface and the base; and
            a second side wall opposite the first side wall between the top surface and the base, wherein the second sidewall slopes away from the first sidewall;
            a channel comprising a first end and a second end, wherein the second end is disposed above the optical window;
        a pressurized gas chamber coupled to the first end of the channel;
        a control valve coupled to the pressurized gas chamber and configured to release pressurized gas within the pressurized gas chamber into the first end of the channel; and
    an optical analyzer optically coupled to the optical window of the sample holder.

2. The system of claim 1, wherein the first side wall is perpendicular to the base.

3. The system of claim 1, further comprising a gas pump coupled to the pressurized gas chamber.

4. The system of claim 1, wherein the channel is located on a lower portion of the first side wall.

5. The system of claim 1, wherein the channel is located on a lower portion of the first side wall and spans the width of the first side wall.

6. The system of claim 1, wherein the sample holder further comprises a moveable cover located toward the inlet of the well.

7. The system of claim 6, wherein the moveable cover comprises a particle sieve.

8. The system of claim 6, wherein the moveable cover comprises an aperture.

9. The system of claim 6, wherein the moveable cover is pivotally, hingedly, or slideably attached to the sample holder.

10. The system of claim 1, wherein the sample holder further comprises a vibration mechanism coupled to the base.

11. The system of claim 1, wherein the optical analyzer comprises a Raman spectrometer, a near infrared spectrometer, a camera, an imaging particle analyzer, or a combination of any of the foregoing.

12. The system of claim 1, further comprising an apparatus having a continuous flow of particles, wherein the inlet of the well is coupled to the continuous flow of particles.

13. A method of analyzing a particle sample from a continuous flow of particles, comprising:
    (a) providing a continuous flow of particles, and the system of claim 1, wherein the inlet of the well is coupled to the continuous flow of particles,
    (b) allowing particles from the continuous flow of particles to settle onto the optical window;
    (c) optically analyzing the settled particles;
    (d) activating the control valve to release pressurized gas into the well and thereby release the settled particles into the continuous flow of particles; and
    (e) closing the control valve.

14. The method of claim 13, further comprising repeating steps (b)-(e) one or more times.

15. The method of claim 13, wherein steps (b)-(e) are repeated at an interval within a range from 100 milliseconds to 1 second.

16. The method of claim 13, wherein the particles comprise pharmaceuticals, fine chemicals, or specialty chemicals.

17. The method of claim 13, wherein optically analyzing comprises spectroscopically analyzing.

18. The method of claim 17, wherein spectroscopically analyzing comprises spectroscopic analysis using Raman spectrometer or a near infrared spectrometer.

19. The method of claim 13, wherein optically analyzing comprises using a camera or an imaging particle analyzer.

20. The method of claim 13, wherein the sample holder further comprises a moveable cover located toward the inlet of the well.

21. The method of claim 20, wherein before allowing the particles to settle, opening the moveable cover to couple the inlet of the well to the continuous flow of particles.

22. The method of claim 21, wherein,
   after allowing the particles to settle, closing the moveable cover; and
   before activating the control valve to release pressurized gas, opening the moveable cover.

23. The method of claim 20, wherein the moveable cover is pivotally, hingedly, or slideably attached to the sample holder.

* * * * *